(12) United States Patent
Hsu

(10) Patent No.: US 8,596,566 B2
(45) Date of Patent: Dec. 3, 2013

(54) BIOMEDICAL HOMOGENIZING DEVICE

(76) Inventor: Yang-Te Hsu, Guishan Township, Taoyuan County (TW)

(*) Notice: Subject to any disclaimer, the term of this patent is extended or adjusted under 35 U.S.C. 154(b) by 87 days.

(21) Appl. No.: 13/350,878

(22) Filed: Jan. 16, 2012

(65) Prior Publication Data
US 2013/0181080 A1   Jul. 18, 2013

(51) Int. Cl.
  *B02C 17/08* (2006.01)
(52) U.S. Cl.
  USPC .......................................... 241/175; 241/174
(58) Field of Classification Search
  USPC ................................... 241/174, 175; 366/216
  See application file for complete search history.

(56) References Cited

U.S. PATENT DOCUMENTS

| | | | | |
|---|---|---|---|---|
| 2,247,978 A | * | 7/1941 | Van Arkel | 366/110 |
| 2,760,729 A | * | 8/1956 | Mittag et al. | 241/137 |
| 2,937,814 A | * | 5/1960 | Joisel | 241/175 |
| 3,212,723 A | * | 10/1965 | Maeder et al. | 241/171 |
| 3,272,443 A | * | 9/1966 | Reiners et al. | 241/153 |
| 4,625,921 A | * | 12/1986 | Blundell | 241/14 |
| 4,779,809 A | * | 10/1988 | Miwa | 241/69 |
| 5,314,125 A | * | 5/1994 | Ohno | 241/175 |
| 5,921,477 A | * | 7/1999 | Tomes et al. | 241/2 |
| 6,020,196 A | | 2/2000 | Hu et al. | |
| 6,086,242 A | * | 7/2000 | Rajamani et al. | 366/217 |
| 6,783,993 B1 | | 8/2004 | Malmquist | |
| 6,880,771 B2 | * | 4/2005 | Deppermann | 241/2 |
| 7,165,734 B2 | | 1/2007 | Bucher | |
| 7,448,566 B2 | * | 11/2008 | Bysouth | 241/175 |
| 7,744,027 B2 | * | 6/2010 | Nagao | 241/170 |
| 8,016,218 B1 | * | 9/2011 | Friedman | 241/175 |
| 8,042,754 B2 | * | 10/2011 | Mahler et al. | 241/175 |
| 2009/0072061 A1 | * | 3/2009 | Yao et al. | 241/175 |

\* cited by examiner

*Primary Examiner* — Faye Franics
(74) *Attorney, Agent, or Firm* — Alan Kamrath; Kamrath IP Lawfirm, P.A.

(57) ABSTRACT

A biomedical homogenizing device a seat, a rotational module, and at least one holding module. The seat has at least one driving wheel set, with each driving wheel set having at least one driving wheel. The rotational module is rotatably mounted on the seat and has a driving shaft and two rotating disks. The driving shaft extends through the at least one driving wheel set, the two rotating disks are respectively and firmly coupled to two ends of the driving shaft, and at least one driven wheel is rotatably mounted on at least one of the two rotating disks to be driven by the driving wheel of the driving wheel set. The at least one holding module is arranged between the two rotating disks and coupled with the at least one driven wheel.

20 Claims, 5 Drawing Sheets

BIOMEDICAL HOMOGENIZING DEVICE

BACKGROUND OF THE INVENTION

1. Field of the Invention

The present invention relates to a biomedical homogenizing device and, more particularly, to a biomedical homogenizing device capable of providing a desirable performance in homogenization.

2. Description of the Related Art

In the research of molecular biology, DNA, RNA or protein samples usually have to be extracted from target materials for further identification or tests, so that a researcher may process a following procedure such as an observation on reactions of the samples to a specific factor. Generally, target materials, such as tissues, cells or germs may be initially mixed with impurities or in an undue size and are impossible for extraction. Therefore, a homogenizing process homogenizing the target materials is necessary.

Conventionally, the homogenizing process is performed such as by centrifugal forces, ultrasonic waves, or mechanical cutting. Taking the homogenizing process of a tissue by mechanical cutting for an example, the tissue is previously received in a vessel, and a tubal blade with slits on its wall is then inserted into the vessel and is turned. Thus, the tissue is cut by the tubal blade, and broken pieces of the tissue are spurted out of the tubal blade through the slits while the tubal blade turns in high speed. However, there may be many tissue pieces that are too large to pass through the slits and that are attached to the inner wall of the tubal blade, which lead to a worse result of the homogenizing process. Besides, these remaining tissue pieces may contaminate the next target material when the tubal blade is used for the next time, since it is hard to entirely clean the tubal blade with the complex structure, thus lowering the accuracy in experimental result of the next target material.

Therefore, most of the present homogenizing processes are performed by centrifuge-homogenizing devices. Taking the homogenizing process of a tissue by a centrifuge-homogenizing device for an example, a ball and the tissue are put into a vessel together, and the vessel is then mounted onto the centrifuge-homogenizing device. Accordingly, the ball may repeatedly dash the tissue to break the tissue into small pieces. However, the vessel receiving the ball and the tissue is merely rotated about one shaft in the conventional centrifuge-homogenizing device. Thus, the homogenizing effect is apparently limited even if the vessel can be driven to rotate about the shaft at a high rotational speed or in a speed range between highest and lowest rotational speeds which are greatly different. Namely, the ball is likely to sink to a bottom of the vessel away from the shaft and cannot dash the tissue throughout the vessel.

It is therefore the primary objective of this invention to provide a biomedical homogenizing device having a high dashing rate toward a target material, to enhance homogenizing efficiency.

SUMMARY OF THE INVENTION

It is therefore the primary objective of this invention to provide a biomedical homogenizing device having a high dashing rate toward a target material, so as to enhance homogenizing efficiency.

Another objective of this invention is providing a biomedical homogenizing device capable of driving a ball inside a tube to thoroughly break a target material inside the tube without contaminating the next target material.

Still another object of this invention is providing biomedical homogenizing device capable of providing a suitable environment at low temperature for a homogenizing process.

The invention discloses a biomedical homogenizing device including a seat, a rotational module, and at least one holding module. The seat has at least one driving wheel set, with each driving wheel set having at least one driving wheel. The rotational module is rotatably mounted on the seat and has a driving shaft and two rotating disks. The driving shaft extends through the at least one driving wheel set, the two rotating disks are respectively and firmly coupled to two ends of the driving shaft, and at least one driven wheel is rotatably mounted on at least one of the two rotating disks to be driven by the driving wheel of the driving wheel set. The at least one holding module is arranged between the two rotating disks and coupled with the at least one driven wheel.

The invention further discloses that a number of the at least one driving wheel set of the seat is two, that these two driving wheel sets are oppositely arranged on two opposite walls of the seat, that each driving wheel set has two driving wheels, and that these two driving wheels have a same number of teeth and are coaxially arranged.

The invention further discloses that a number of the at least one driven wheel of each rotating disk is two, that these two driven wheels are arranged on a diameter line passing through a center of the respective rotating disk, and that the two diameter lines of the two rotating disks are non-parallel to each other.

The invention further discloses that the driving shaft extends through the two driving wheel set by the two ends of the driving shaft respectively, and a rotational power source connects with one of the ends of the driving shaft.

The invention further discloses that each driven wheel has a rotated part rotatable relatively to the respective rotating disk and a coupling part protruding from an inner surface of the respective rotating disk, with the coupling part adaptive to couple with a respective one of the at least one holding module.

The invention further discloses that at least one coupling member is rotatably arranged on at least one of the rotating disks, and that the at least one coupling member is opposite to the at least one driven wheel.

The invention further discloses that each holding module is coupled with a respective one of the at least one driven wheel and a respective one of the at least one coupling member by two opposite ends.

The invention further discloses that a magnet is disposed on a circumferential wall of the driving shaft and annularly surrounding the driving shaft.

The invention further discloses that the seat is in a shape of a housing and has an air conditioner inside.

The invention further discloses that each of the two ends of the driving shaft has an engaging portion extending and coupling with a respective one of the two rotating disks, and that each end of the driving shaft further provides a C-ring abutting against an outer side of the respective rotating disk.

The invention further discloses that a plurality of compartments is formed in the holding module, with a lid capable of covering openings of the compartments.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
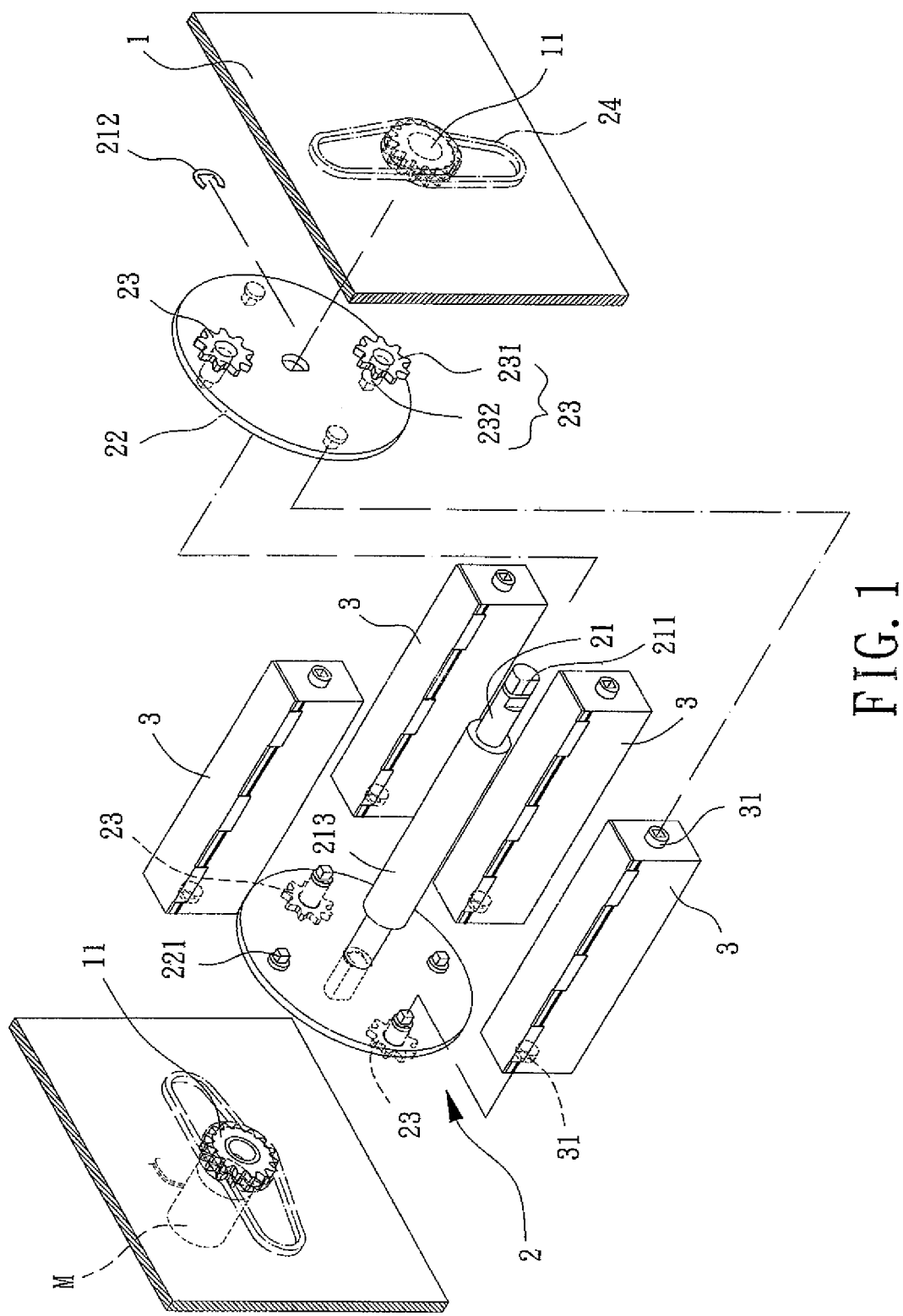
FIG. 1 shows a perspective and exploded view of a biomedical homogenizing device according to a preferable embodiment of the invention.

In the various figures of the drawings, the same numerals designate the same or similar parts. Furthermore, when the terms "inner," "outer" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

Please refer to FIG. 1. A biomedical homogenizing device according to a preferable embodiment of the invention is shown, which includes a seat 1, a rotational module 2 rotatably mounted on the seat 1, and at least one holding module 3 rotatably mounted on and driven by the rotational module 2. A tube 4 receiving a target material and a ball 41 can be held by the at least one holding module 3. The at least one holding module 3 can be driven to revolve as well as to rotate about a center axis of the rotational module 2, to enhance the moving range and frequency of the ball 41 in the tube 4 and to achieve an improved homogenizing effect. In this preferable embodiment, a number of the at least one holding module 3 is four. However, the number of the at least one holding module 3 is not limited.

The seat 1 is adapted to support or receive the rotational module 2, and the shape of the seat 1 is thus not limited. Specifically, as shown in FIG. 2, the seat 1 is preferably a housing with a receiving room "S" for the rotational module 2 to be assembled therein, with an opening "W" arranged in the wall of the housing and communicating with the receiving room "S," and with a cover "B" capable of covering the opening "W" to seal the receiving room "S."

Figure 2:
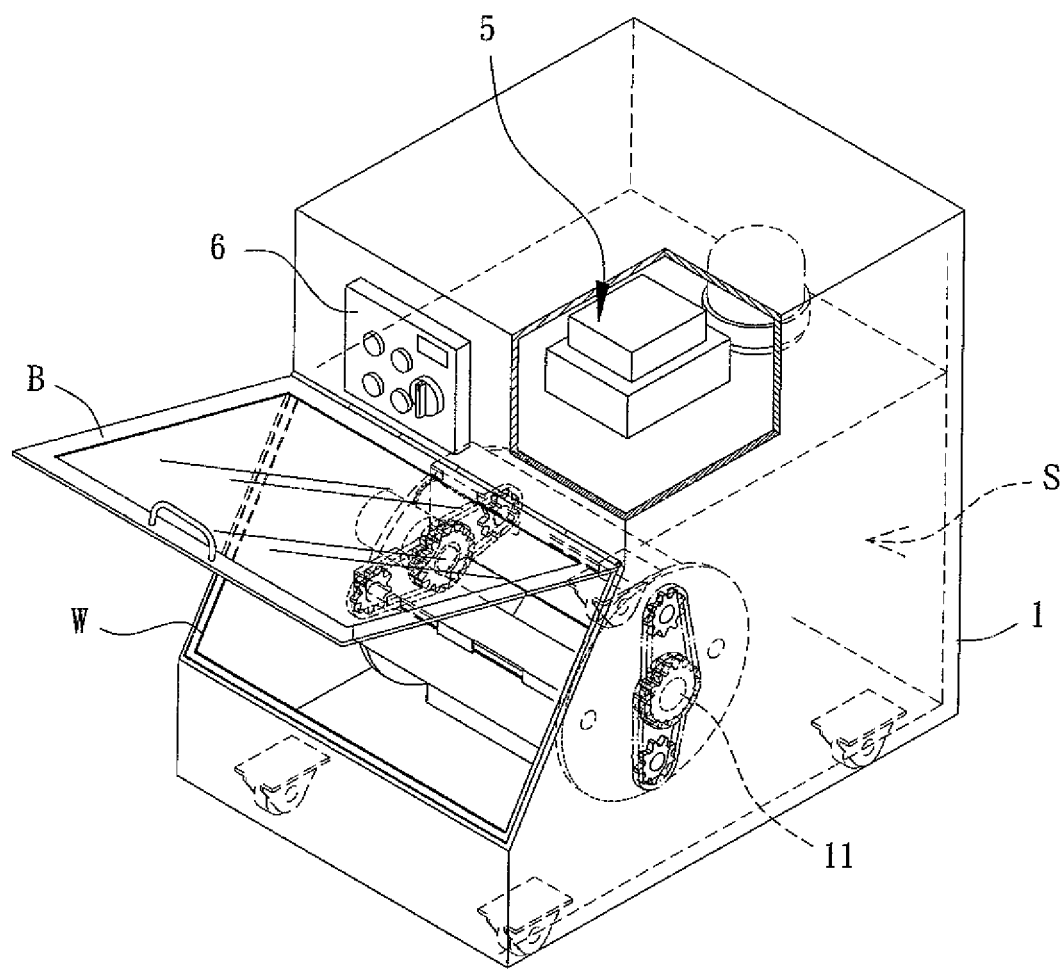
FIG. 2 shows a perspective and assembled view of the biomedical homogenizing device.

Referring to FIGS. 1 and 2, the seat 1 has at least one driving wheel set 11, with each driving wheel set 11 having at least one driving wheel. In this embodiment, the number of the at least one driving wheel set 11 is two, with these two driving wheel sets 11 oppositely and firmly mounted on two opposite walls of the seat 1. Furthermore, in this embodiment, a number of the at least one driving wheel of each driving wheel set 11 is two, and these two driving wheel are preferably two gear wheels having the same number of teeth and coaxially arranged. Please note that the at least one driving wheel of the at least one driving wheel set 11 is provided to drive the at least one holding module 3. Therefore, the arrangement of the at least one driving wheel set 11 is not limited as long as a total number of the at least one driving wheel of the at least one driving wheel set 11 is equal to the number of the at least one holding module 3 for the at least one driving wheel to respectively drive the at least one holding module 3. For example, while there are three holding modules 3 mounted on the rotational module 2, there can be only one driving wheel set 11 having three driving wheels or two driving wheel sets 11 with one driving wheel and two driving wheels respectively.

The rotational module 2 is rotatably mounted on the seat 1 and arranged between the two driving wheel sets 11, while the number of the at least one driving wheel set 11 is two. The rotational module 2 has a driving shaft 21 and two rotating disks 22. The driving shaft 21 extends through the two driving wheel sets 11 by two ends respectively, with one of the two ends of the driving shaft 21 connecting with a rotational power source "M" adaptive to turn the rotational module 2. The two rotating disks 22 are firmly coupled to the two ends of the driving shaft 21 to turn with the driving shaft 21. In this embodiment, each of the two ends of the driving shaft 21 has an engaging portion 211 extending and coupling with a respective one of the two rotating disks 22, while each end of the driving shaft 21 further provides a C-ring 212 abutting against an outer side of the respective rotating disk 22 to ensure that the rotating disk 22 is firmly coupled with the engaging portion 211. Furthermore, it is preferable to dispose a magnet 213 on the circumferential wall of the driving shaft 21 and, more preferably, annularly surrounding the driving shaft 21, to attract the ball 41 while the ball 41 is made of magnetic conductive material.

Specifically, there is at least one driven wheel 23 rotatably mounted on at least one of the two rotating disks 22 and coupled with the at least one holding module 3. The driven wheel 23 can be driven to revolve relatively to the rotating disk 22, and the way to revolve the driven wheel 23 is using a gear wheel as the driven wheel 23 and linking the driven wheel 23 and a respective one of the at least one driving wheel of the at least one driving wheel set 11 by a linking member 24 such as a roller chain in this embodiment. Preferably, the diameter of the driving wheel of the driving wheel set 11 is larger than that of the driven wheel 23, to drive the driven wheel 23 to revolve faster than the revolving speed of the driving shaft 21. However, other conventional ways such as using a belt instead of the roller chain as the linking member 24 or directly engaging the teeth of the driven wheel 23 with the teeth of the driving wheel of the driving wheel set 11 without using the linking member 24 is also practicable. Furthermore, the at least one driving wheel set 11 can also be omitted if there is a fixed gear wheel formed on the rotating disk 22 with teeth of the fixed gear wheel engaging with that of the driven wheel 23. In this embodiment, each of the rotating disks 22 has two driven wheels 23 arranged on a diameter line passing through the center of the respective rotating disk 22, while the two diameter lines of the two rotating disks 22 are preferably non-parallel to each other as shown in FIG. 1. Moreover, there is at least one coupling member 221 rotatably arranged on at least one of the rotating disks 22. Specifically, the at least one coupling member 221 is arranged on one of the rotating disks 22 oppositely to the at least one driven wheel 23 on the other one of the rotating disks 22 in an axial direction of the driving shaft 21, so that the driven wheel 23 and coupling member 221 couple with the holding module 3 in a sandwiched way. Particularly, each one of the at least one driven wheel 23 has a rotated part 231 rotatable relatively to the respective rotating disk 22 and a coupling part 232 protruding from an inner surface of the rotating disk 22. The rotated part 231 is adaptive to be driven by the driving wheel of the driving wheel set 11, and the coupling part 232 is adaptive to couple with the holding module 3.

Figure 3:
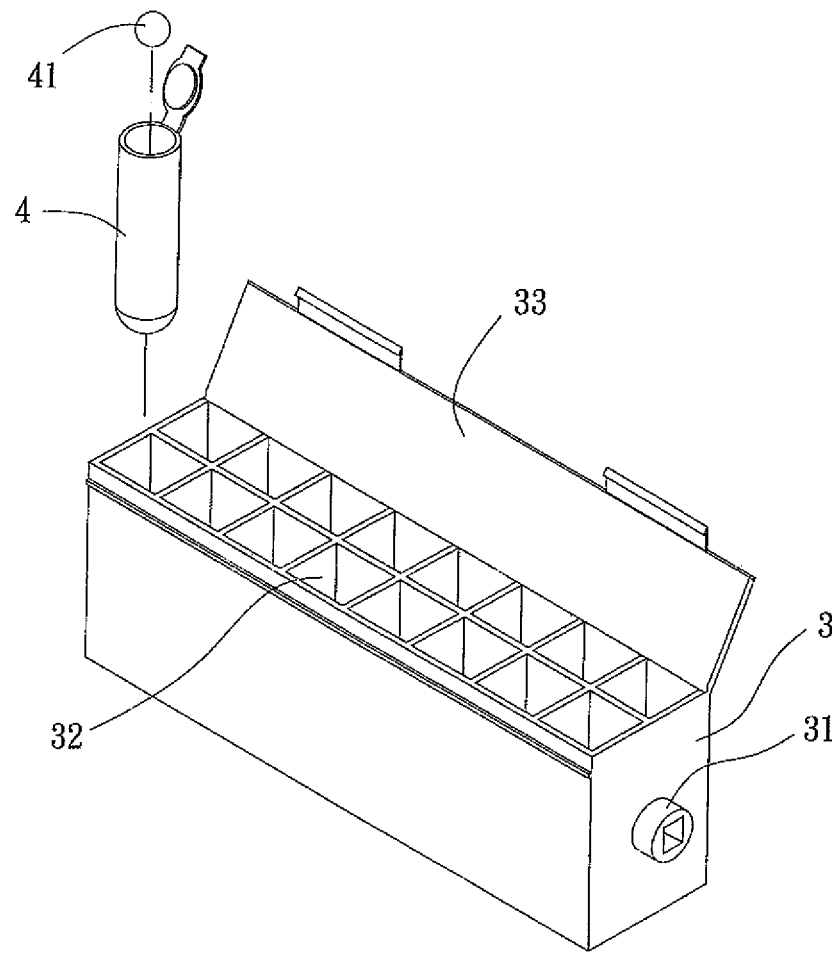
FIG. 3 shows a perspective and exploded view of a holding module and a tube of the biomedical homogenizing device.

Referring to FIGS. 1 through 3, the at least one holding module 3 is sandwiched by the at least one driven wheel 23 and the coupling member 221, with two opposite ends of each holding module 3 having two noncircular holes 31 respectively. Thus, a respective one of the at least one driven wheel 23 is firmly inserted into one of the noncircular holes 31 by the coupling part 232, and a respective one of the at least one coupling member 221 is firmly inserted into the other one of the noncircular holes 31. In this embodiment, the holding module 3 is in a shape of a box as shown in FIG. 3, with a plurality of compartments 32 formed in the box to respectively and fixedly receive a plurality of tubes 4. Besides, a lid 33 for covering openings of the compartments 32 is also used to prevent the tubes 4 from falling out of the holding module 3.

Particularly, when the seat 1 is in the shape of a housing, there can be an air conditioner 5 received in the seat 1 to control the environment inside the seat 1, which is preferably at a temperature of 4° C. Besides, a control interface 6 electrically connecting with the rotational power source "M" and the air conditioner 5 can also be used to control the rotation of the rotational module 2 and the air conditioner 5.

Figure 4:
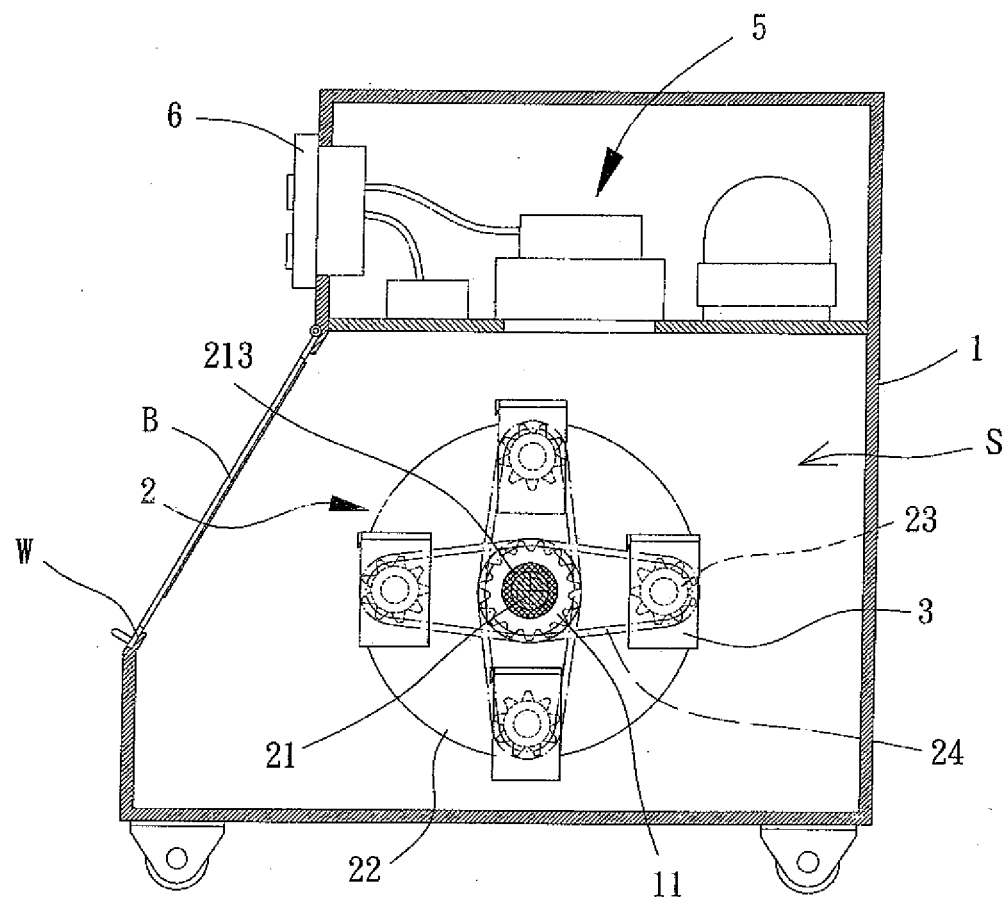
FIG. 4 shows a cross-sectional view of the biomedical homogenizing device.
Figure 5:
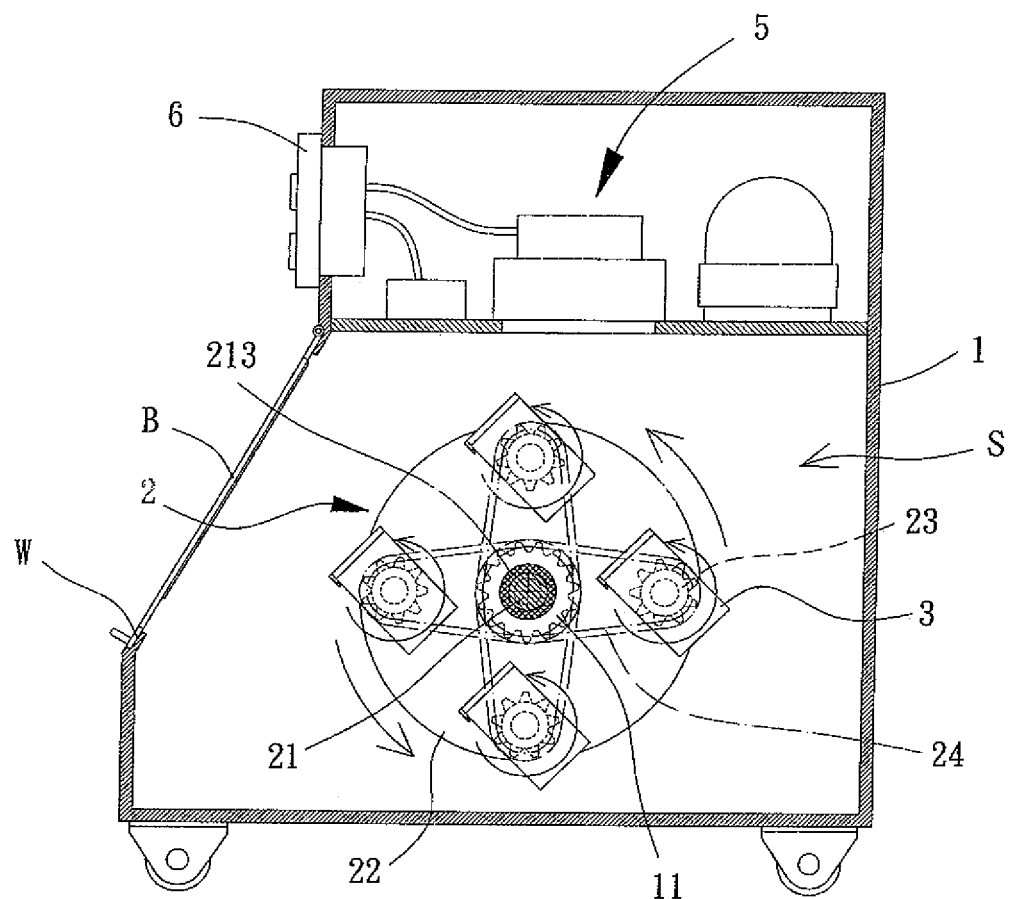
FIG. 5 shows a cross-sectional view of the biomedical homogenizing device in operation.

In operation, referring to FIGS. 4 and 5, a target material and at least one ball 41 are previously put into the tube 4, and, then, the tube 4 is inserted into one of the compartments 32 of the holding module 3. Finally, the user may set up the rotation speed of the rotational module 2 and the temperature of the environment through the control interface 6, to perform the homogenizing process. Accordingly, with the rotational power source "M" driving the driving shaft 21 of the rotational module 2, the rotating disks 22 revolve to rotate the holding module 3 about the driving shaft 21. Besides, through the driving wheel of the driving wheel set 11, the linking member 24 and the driven wheel 23, the holding module 3 is revolved relatively to the rotating disks 22. Therefore, the holding module 3 is not only shifted but also revolved, and, thus, the ball 41 inside the tube 4 can thoroughly and repeatedly roll in the tube 4 to effectively break and homogenize the target material. Consequently, no matter what rotational speed the rotational module 2 is, the target material can still be effectively and thoroughly homogenized, since the movement of the holding module 3 is violent and various.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A biomedical homogenizing device comprising:
a seat including a first driving wheel, wherein the seat is in a shape of a housing defining a receiving room having a removable cover;
a rotational module rotatably mounted on the seat inside of the receiving room and having a driving shaft and first and second rotating disks, wherein the driving shaft extends through the first driving wheel, the first and second rotating disks are respectively and firmly coupled to two ends of the driving shaft, and a first driven wheel is rotatably mounted on the first rotating disk to be driven by the first driving wheel;
a first holding module arranged between the first and second rotating disks and coupled with the first driven wheel; and
an air conditioner inside of the receiving room.

2. The biomedical homogenizing device as claimed in claim 1, further comprising:
a second holding module arranged between the first and second rotation disks; and
a second driven wheel rotatably mounted on the first rotating disk; and
a second driving wheel included in the seat, wherein the second holding module is coupled with the second driven wheel, wherein the first driven wheel is driven by the first driving wheel, wherein the second driven wheel is driven by the second driving wheel, and wherein the first and second driving wheels have a same number of teeth and are coaxially arranged.

3. The biomedical homogenizing device as claimed in claim 2, further comprising:
a third holding module arranged between the first and second rotation disks;
a third driving wheel with the third driving wheel and the first and second driving wheels oppositely arranged on two opposite walls of the seat, with the driving shaft extending through the third driving wheel; and
a third driven wheel rotatably mounted on the second rotating disk, with the third holding module coupled with the third driven wheel, wherein the first and second driven wheels and the third driven wheel are arranged on diameter lines passing through a center of the first and second rotating disks, and wherein the diameter lines of the first and second rotating disks are non-parallel to each other.

4. The biomedical homogenizing device as claimed in claim 3, wherein the driving shaft extends through the first and second driving wheels and the third driving wheel by the two ends of the driving shaft respectively, and a rotational power source connects with one of the two ends of the driving shaft.

5. The biomedical homogenizing device as claimed in claim 1, wherein the first driven wheel has a rotated part rotatable relatively to the first rotating disk and a coupling part protruding from an inner surface of the second rotating disk, with the coupling part coupling with the first holding module.

6. The biomedical homogenizing device as claimed in claim 1, wherein at least one coupling member is rotatably arranged on the second rotating disk, and the at least one coupling member is opposite to the first driven wheel.

7. The biomedical homogenizing device as claimed in claim 6, wherein the first holding module is coupled with the first driven wheel and the at least one coupling member by two opposite ends.

8. The biomedical homogenizing device as claimed in claim 1, wherein a magnet is disposed on a circumferential wall of the driving shaft and annularly surrounding the driving shaft.

9. The biomedical homogenizing device as claimed in claim 1, wherein each of the two ends of the driving shaft has an engaging portion extending and coupling with the first and second rotating disks respectively, and each of the two ends of the driving shaft further provides a C-ring abutting against an outer side of the first and second rotating disks respectively.

10. The biomedical homogenizing device as claimed in claim 1, wherein a plurality of compartments is formed in the first holding module, with a lid capable of covering openings of the plurality of compartments.

11. The biomedical homogenizing device as claimed in claim 1, further comprising a second holding module arranged between the first and second rotating disks, wherein the seat includes a second driving wheel, wherein the first and second driving wheels are oppositely arranged in two opposite walls of the seat, with the rotational module located intermediate the two opposite walls of the seat, wherein a driven wheel is rotatably mounted on the second rotating disk to be driven by the second driving wheel; and wherein the second holding module is coupled with the driven wheel of the second rotating disk.

12. The biomedical homogenizing device as claimed in claim 11, further comprising first and second coupling members on the first and second rotating disks respectively, with the first holding module rotatably coupled with the second coupling member and with the second holding module rotatably coupled with the first coupling member.

13. The biomedical homogenizing device as claimed in claim 12, further comprising third and fourth holding modules arranged between the first and second rotating disks, wherein another driven wheel is rotatably mounted on the first rotating disk, with the driven wheels of the first rotation disk arranged on opposite ends of a diameter line passing through a center of the first rotating disk; wherein another driven wheel is rotatably mounted on the second rotating disk, with the driven wheels of the second rotating disk arranged on opposite ends of a diameter line passing through a center of the second rotating disk; wherein the diameter lines of the first and second rotating disks are non-parallel to each other, with the driven wheels of the first rotating disk rotatably connected to the first driving wheel, with the driven wheels of the second rotating disk rotatably connected to the second driving wheel, with the third holding module coupled with the other driven wheel of the first rotating disk and with the fourth holding module coupled with the other driven wheel of the second rotating disk.

14. The biomedical homogenizing device as claimed in claim 13, wherein the seat includes third and fourth driving wheels, with the first and third driving wheels and the second and fourth driving wheels having a same number of teeth and coaxially arranged, with the driven wheel and the other driven wheel of the first rotating disk rotatably connected to the first and third driving wheels respectively, with the driven wheel and the other driven wheel of the second rotating disk rotatably connected to the second and fourth driving wheels respectively.

15. The biomedical homogenizing device as claimed in claim 14, further comprising third and fourth coupling members on the first and second rotating disks respectively, with the third holding module rotatably coupled with the fourth coupling member and with the fourth holding module rotatably coupled with the third coupling member.

16. The biomedical homogenizing device as claimed in claim 11, further comprising third and fourth holding modules arranged between the first and second rotating disks, wherein another driven wheel is rotatably mounted on the first rotating disk, with the driven wheels of the first rotation disk arranged on opposite ends of a diameter line passing through a center of the first rotating disk; wherein another driven wheel is rotatably mounted on the second rotating disk, with the driven wheels of the second rotating disk arranged on opposite ends of a diameter line passing through a center of the second rotating disk; wherein the diameter lines of the first and second rotating disks are non-parallel to each other, with the driven wheels of the first rotating disk rotatably connected to the first driving wheel, with the driven wheels of the second rotating disk rotatably connected to the second driving wheel, with the third holding module coupled with the other driven wheel of the first rotating disk and with the fourth holding module coupled with the other driven wheel of the second rotating disk.

17. The biomedical homogenizing device as claimed in claim 16, wherein the seat includes third and fourth driving wheels, with the first and third driving wheels and the second and fourth driving wheels having a same number of teeth and coaxially arranged, with the driven wheel and the other driven wheel of the first rotating disk rotatably connected to the first and third driving wheels respectively, with the driven wheel and the other driven wheel of the second rotating disk rotatably connected to the second and fourth driving wheels respectively.

18. The biomedical homogenizing device as claimed in claim 11, wherein the first driven wheel is arranged on a diametric line passing through a center of the first rotating disk, wherein the second driven wheel is arranged on a diametric line passing through a center of the second rotating disk, wherein the diametric lines of the first and second rotating disks are non-parallel to each other.

19. The biomedical homogenizing device as claimed in claim 18, wherein the driving shaft extends through the first and second driving wheels and the third driving wheel by the two ends of the driving shaft respectively, and a rotational power source connects with one of the two ends of the driving shaft.

20. The biomedical homogenizing device as claimed in claim 18, further comprising third and fourth holding modules arranged between the first and second rotating disks, wherein another driven wheel is rotatably mounted on the first rotating disk, with the driven wheels of the first rotation disk arranged on opposite ends of a diameter line passing through a center of the first rotating disk; wherein another driven wheel is rotatably mounted on the second rotating disk, with the driven wheels of the second rotating disk arranged on opposite ends of a diameter line passing through a center of the second rotating disk; wherein the diameter lines of the first and second rotating disks are non-parallel to each other, with the driven wheels of the first rotating disk rotatably connected to the first driving wheel, with the driven wheels of the second rotating disk rotatably connected to the second driving wheel, with the third holding module coupled with the other driven wheel of the first rotating disk and with the fourth holding module coupled with the other driven wheel of the second rotating disk.

* * * * *